United States Patent [19]
Paciorek et al.

[11] Patent Number: 5,779,774
[45] Date of Patent: Jul. 14, 1998

[54] RUST INHIBITING PHOSPHATE ESTER FORMULATIONS

[76] Inventors: Kazimiera J. L. Paciorek, 1425 Seacrest Dr., Corona Del Mar, Calif. 92625; Steven R. Masuda, 29322 Crown Ridge, Laguna Niguel, Calif. 92656

[21] Appl. No.: 819,541

[22] Filed: Mar. 17, 1997

Related U.S. Application Data

[60] Provisional application No. 60/

[51] Int. Cl.$^6$ .................... C23F 11/10; C10M 129/68; C10M 137/04

[52] U.S. Cl. .................... 106/14.41; 44/375; 44/382; 106/14.12; 106/14.26; 208/14; 252/389.2

[58] Field of Search .................... 106/14.41, 14.12, 106/14.26; 252/389.2; 44/375, 382; 208/14

[56] References Cited

U.S. PATENT DOCUMENTS

| | | | |
|---|---|---|---|
| 3,071,549 | 1/1963 | Star | 252/78.5 |
| 3,468,802 | 9/1969 | Nail | 252/78.5 |
| 3,780,145 | 12/1973 | Malec | 558/211 |
| 3,931,023 | 1/1976 | Dounchis | 252/78.5 |
| 4,061,695 | 12/1977 | Tai et al. | 558/164 |
| 4,318,817 | 3/1982 | Huebner | 252/78.5 |
| 4,461,713 | 7/1984 | Anzenberger, Sr. | 252/78.5 |
| 5,205,951 | 4/1993 | Mackinnon | 252/78.5 |
| 5,464,551 | 11/1995 | Deetman | 252/78.5 |
| 5,630,964 | 5/1997 | Babaian-Kibala et al. | 252/389.23 |

*Primary Examiner*—Anthony Green

[57] ABSTRACT

Mixtures of alkylaromatic secondary phosphate and tertiary phosphate esters prepared by reaction of phosphonyl chloride and primary phosphonyl chlorides with alkylaromatic phenols are disclosed as rust inhibiting additives for hydrocarbon based fluids.

6 Claims, No Drawings

RUST INHIBITING PHOSPHATE ESTER FORMULATIONS

This application claims the benefit of U.S. Provisional Application Ser. No 60/014.686, filed Apr. 2. 1996.

FIELD OF THE INVENTION

The invention relates to mixtures of tertiary and secondary alkyl substituted aromatic phosphate esters for use as rust inhibiting additives in hydrocarbon fluids.

BACKGROUND OF THE INVENTION

Hydrocarbon fluids when used in environments where the presence of moisture leads to rust formation require to contain rust inhibiting additives. The commonly employed inhibitors such as barium dinonylnaphthalene sulfonate and related composition need to be replaced in view of the presence of environmentally undesirable heavy metals. Furthermore barium dinonylnaphthalene sulfonate itself is susceptible to barium carbonate precipitation on reaction with atmospheric carbon dioxide and thus depletion of the rust inhibiting ingredient. The additives disclosed in the present invention are environmentally friendly and in the actual tests are proven to be more effective than the currently used materials. This invention pertains specifically to mixtures of phosphate esters soluble in hydrocarbon fluids and prepared by a partial esterification process using long chain alkylaromatic phenols to give rust inhibiting additives soluble in hydrocarbon fluids. This is to the best of our knowledge a novel, previously unknown approach to rust inhibiting additives for hydrocarbon fluids.

SUMMARY OF THE INVENTION

It is the principal object of this invention, therefore to provide rust inhibiting additives to be used in hydrocarbon fluids such as mineral oils e.g. Mil-H5606, synthetic poly-alphaolefins e.g. Mil-H-83282 and a new class of synthetics represented by the Pennzane (product of Pennzoil Products Co.) family of materials.

Another object of the invention is to provide the rust inhibiting mixtures of tertiary and secondary phosphate esters. Additional object of the invention is to provide the process for preparing the rust inhibiting mixtures of the tertiary and secondary phosphate esters. Other objects and advantages of the invention will become apparent to those skilled in the art upon consideration of the accompanying disclosure.

DESCRIPTION OF THE PREFERRED EMBODIMENTS

The present invention resides in mixtures of tertiary and secondary phosphate esters represented by the following:

a) $(RC_6H_4O)_3P(O)$, $(RC_6H_4O)_2P(O)(OH)$ and
b) $(RC_6H_4O)_2(R'C_6H_4O)P(O)$, $(RC_6H_4O)(R'C_6H_4O)P(O)(OH)$ wherein R and R' are selected from the groups $C_nH_{2n+1}$, wherein n ranges from 1 to 20. R' can be also H.

The general reactions are given below:

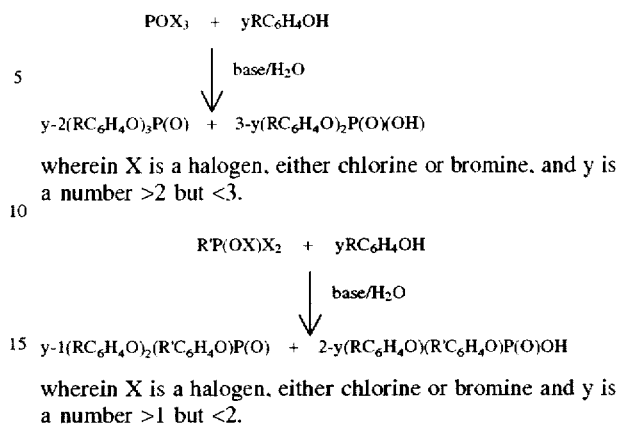

wherein X is a halogen, either chlorine or bromine, and y is a number >2 but <3.

$$R'P(OX)X_2 + yRC_6H_4OH$$
$$\downarrow \text{base/H}_2O$$
$$y-1(RC_6H_4O)_2(R'C_6H_4O)P(O) + 2-y(RC_6H_4O)(R'C_6H_4O)P(O)OH$$

wherein X is a halogen, either chlorine or bromine and y is a number >1 but <2.

The processes leading to the phosphate esters are preferably conducted in aromatic solvents such as benzene or toluene or oxygenated solvents such as diethyl ether in the presence of a base such as tertiary amine using lower than the equivalent quantities of the phenol. The reaction is performed preferably at 25° to 90° C. under an inert gas such as nitrogen, helium or argon. The reaction periods range from 4 to 24 hours. The halophosphorus reagents and phenols are commercially available.

EXAMPLE I

Under nitrogen atmosphere to a stirred solution of $POCl_3$ (0.61 g, 3.98 mmol) and $C_{15}H_{31}C_6H_4OH$ (2.50 g, 8.21 mmol) in benzene (15 mL) was added triethylamine (2.50 g, 24.7 mmol) in benzene (10 mL) over 10 min. The reaction mixture was heated at 65°–75° C. over a period of 20 hours. After cooling the produced triethylamine hydrochloride (1.13 g) was filtered off. To the filtrate was added diethyl ether and the organic layer was washed with dilute hydrochloric acid, water and dried over anhydrous magnesium sulfate to give, after solvent removal, 2.6 g (95% yield) of low melting solid (mp 30°–33° C.) consisting of 92% of $(C_{15}H_{31}C_6H_4O)_2P(O)OH$ and 8% of $(C_{15}H_{31}C_6H_4O)_3P(O)$ by weight. This material was evaluated for its rust inhibiting action. The data are given in Example III in Table 1.

EXAMPLE II

Under nitrogen atmosphere to a stirred solution of $Cl_2P(O)OC_6H_5$ (1.80 g, 8.53 mmol) and $C_{15}H_{31}C_6H_4OH$ (2.89 g, 9.49 mmol) in benzene (20 mL) was added triethylamine (3.84 g, 38.0 mmol) in benzene (15 mL) over 10 min. Subsequently, the reaction mixture was heated at 75°–80° C. for 21 hours. After cooling the produced triethylamine hydrochloride (1.3 g) was filtered off. To the filtrate was added diethyl ether and the organic layer was washed with dilute hydrochloric acid and water, then dried over anhydrous magnesium sulfate to give, after solvent removal, an oil (4.1 g, 98% yield) consisting of 17% of $(C_6H_5O)P(O)(OC_6H_4C_{15}H_{31})_2$ and 83% of $(C_6H_5O)(C_{15}H_{31}C_6H_4O)P(O)OH$ by weight. This material was evaluated for its rust inhibiting action. The data are given in Example III, Table 1.

EXAMPLE III

The additives disclosed in Examples II and III were evaluated for their rust inhibiting action in mineral oil based fluid, Mil-H-5606; synthetic polyalphaolefin fluid Mil-H-83282; and new family of fluids, multiply-alkylated cyclopentanes, "Pennzanes" (product of Pennzoil Products Co.). The results of these evaluations are summarized in Table 1.

TABLE 1

Results of Rust Inhibiting Evaluations[a]

| Fluid | Additive | Wt % | Corrosion side1/side2 |
|---|---|---|---|
| Mil-H-6083[b] | BSN + g co-additive | 1.0 | 0/0 |
| Mil-H-5606 | none | 0 | 40/40 |
| Mil-H-5606 | 92%(ArO)$_2$P(O)OH/8%(ArO)$_3$P(O)[c] | 0.5 | 0/0 |
| Mil-H-46170[d] | BSN | 1.5 | 0/0 |
| Mil-H-83282 | none | 0 | 50/30 |
| Mil-H-83282 | 92%(ArO)$_2$(O)OH/8%(ArO)$_3$P(O)[c] | 0.5 | 0/0 |
| Pennzane X2000 | none | 0 | 60/50 |
| Pennzane X2000 | 92%(ArO)$_2$P(O)OH/8%(ArO)$_3$P(O)[c] | 0.5 | 0/0 |
| Mil-H-6083[b] | BSN + g co-additive | 1.0 | 0/0 |
| Mil-H-5606 | none | 0 | 70/45 |
| Mil-H-5606 | 83%(C$_6$H$_5$O)P(O)(OAr)OH/17%(C$_6$H$_5$O)P(O)(OAr)$_2$[c] | 0.5 | 0/0 |
| Mil-H-46170[d] | BSN | 1.5 | 0/0 |
| Mil-H-83282 | none | 0 | 45/20 |
| Mil-H-83282 | 83%(C$_6$H$_5$O)P(O)(OAr)OH/17%(C$_6$H$_5$O)P(O)(OAr)$_2$[c] | 0.5 | 0/0 |

Industrial Application

In summary, the invention is embodied in a rust inhibitor for hydrocarbon based fluids consisting essentially of a mixture of compounds comprising (a) (RC$_6$H$_4$O)$_2$P(O)OH wherein R is selected from groups having a general formula C$_n$H$_{2n+1}$ wherein n is an integer from 1 to 20 inclusive, and (b) (RC$_6$H$_4$O)$_3$P(O) wherein R is selected from groups having a general formula C$_n$H$_{2n+1}$ wherein n is an integer from 1 to 20 inclusive, and in rust resistant hydrocarbon based fluids containing said rust inhibitor. In one embodiment, the rust inhibitor consists essentially of from 2% to 98% of (C$_{15}$H$_{31}$C$_6$H$_4$O)$_2$P(O)OH and 98% to 2% of (C$_{15}$H$_{31}$C$_6$H$_4$O)$_3$P(O).

The rust inhibitor may consist essentially of (a) (RC$_6$H$_4$O)(R'C$_6$H$_4$O)P(O)(OH) wherein R is selected from groups having a general formula C$_n$H$_{2n+1}$ wherein n is an integer from 1 to 20 inclusive, wherein R' is hydrogen or is selected from groups having a general formula C$_n$H$_{2n+1}$ wherein n is an integer from 1 to 20 inclusive, and (b) R(C$_6$H$_4$O)$_2$(R'C$_6$H$_4$O)P(O) wherein R is selected from groups having a general formula C$_n$H$_{2n+1}$ wherein n is an integer from 1 to 20 inclusive, wherein R' is hydrogen or is selected from groups having a general formula C$_n$H$_{2n+1}$ wherein n is an integer from 1 to 20 inclusive.

The invention has application in the chemical process industries and in the manufacture of environment friendly, free of heavy metals, additives for hydrocarbon based fluids. The use of the additives, herein disclosed, provides for rust protection.

What is claimed is:

1. A rust inhibitor for hydrocarbon based fluids consisting essentially of a mixture of compounds comprising:

(a) (RC$_6$H$_4$O)$_2$P(O)OH wherein R is selected from groups having a general formula C$_n$H$_{2n+1}$ wherein n is an integer from 1 to 20 inclusive, and (b) (RC$_6$H$_4$O)$_3$P(O) wherein R is selected from groups having a general formula C$_n$H$_{2n+1}$ wherein n is an integer from 1 to 20 inclusive.

2. A rust inhibitor for hydrocarbon based fluids consisting essentially of:

(a) (RC$_6$H$_4$O)(R'C$_6$H$_4$O)P(O)(OH) wherein R is selected from groups having a general formula C$_n$H$_{2n+1}$ wherein n is an integer from 1 to 20 inclusive, wherein R' is hydrogen or is selected from groups having a general formula C$_n$H$_{2n+1}$ wherein n is an integer from 1 to 20 inclusive, and (b) (RC$_6$H$_4$O)$_2$(R'C$_6$H$_4$O)P(O) wherein R is selected from groups having a general formula C$_n$H$_{2n+1}$ wherein n is an integer from 1 to 20 inclusive, wherein R' is hydrogen or is selected from groups having a general formula C$_n$H$_{2n+1}$ wherein n is an integer from 1 to 20 inclusive.

3. A rust inhibited hydrocarbon based fluid composition comprising at least one hydrocarbon based fluid and a rust inhibitor, the rust inhibitor consisting essentially of:

(a) (RC$_6$H$_4$O)$_2$P(O)OH wherein R is selected from groups having a general formula C$_n$H$_{2n+1}$ wherein n is an integer from 1 to 20 inclusive, and (b) (RC$_6$H$_4$O)$_3$P(O) wherein R is selected from groups having a general formula C$_n$H$_{2n+1}$ wherein n is an integer from 1 to 20 inclusive.

4. The composition of claim 3 wherein the hydrocarbon based fluid is selected from the group consisting of mineral oil based hydrocarbon based fluid, synthetic polyalphaolefin fluid and multiply-alkylated cyclopentanes.

5. A rust inhibited hydrocarbon fluid composition comprising at least one hydrocarbon fluid and a rust inhibitor, the rust inhibitor consisting essentially of:

(a) (RC$_6$H$_4$O)(R'C$_6$H$_4$O)P(O)(OH) wherein R is selected from groups having a general formula C$_n$H$_{2n+1}$ wherein n is an integer from 1 to 20 inclusive, wherein R' is hydrogen or is selected from groups having a general formula C$_n$H$_{2n+1}$ wherein n is an integer from 1 to 20 inclusive, and (b) (RC$_6$H$_4$O)$_2$(R'C$_6$H$_4$O)P(O) wherein R is selected from groups having a general formula C$_n$H$_{2n+1}$ wherein n is an integer from 1 to 20 inclusive, wherein R' is hydrogen or is selected from groups having a general formula C$_n$H$_{2n+1}$ wherein n is an integer from 1 to 20 inclusive.

6. The composition of claim 5 wherein the hydrocarbon fluid is selected from the group consisting of mineral oil based hydrocarbon fluid, synthetic polyalphaolefin fluid and multiply-alkylated cyclopentanes.

\* \* \* \* \*